US011154359B2

(12) United States Patent
Cattin et al.

(10) Patent No.: US 11,154,359 B2
(45) Date of Patent: Oct. 26, 2021

(54) BONE CUT TREATMENT

(71) Applicant: ADVANCED OSTEOTOMY TOOLS—AOT AG, Basel (CH)

(72) Inventors: Philippe C. Cattin, Windisch (CH); Alfredo E. Bruno, Biel-Benken (CH); Azagen Mootien, Ranzwiller (FR)

(73) Assignee: ADVANCED OSTEOTOMY TOOLS—AOT AG, Basel (CH)

( * ) Notice: Subject to any disclaimer, the term of this patent is extended or adjusted under 35 U.S.C. 154(b) by 321 days.

(21) Appl. No.: 15/757,796

(22) PCT Filed: Sep. 6, 2016

(86) PCT No.: PCT/EP2016/070988
§ 371 (c)(1),
(2) Date: Mar. 6, 2018

(87) PCT Pub. No.: WO2017/042168
PCT Pub. Date: Mar. 16, 2017

(65) Prior Publication Data
US 2018/0256254 A1 Sep. 13, 2018

(30) Foreign Application Priority Data
Sep. 7, 2015 (EP) .................................... 15184104

(51) Int. Cl.
*A61B 18/20* (2006.01)
*A61B 18/00* (2006.01)
(Continued)

(52) U.S. Cl.
CPC ............ *A61B 18/20* (2013.01); *A61B 18/203* (2013.01); *A61B 17/16* (2013.01);
(Continued)

(58) Field of Classification Search
USPC .......................................................... 606/18
See application file for complete search history.

(56) References Cited

U.S. PATENT DOCUMENTS 3,910,276 A 10/1975 Polanyi
4,473,074 A 9/1984 Vassiliadis
(Continued)

FOREIGN PATENT DOCUMENTS

CN 1070816 A 4/1993
CN 104302234 A 1/2015
(Continued)

OTHER PUBLICATIONS

Extended European Search Report for European Patent Application No. 19186569.0 dated Dec. 6, 2019.
(Continued)

*Primary Examiner* — Nicole F Lavert
(74) *Attorney, Agent, or Firm* — Kratz, Quintos & Hanson, LLP

(57) ABSTRACT

A method of cutting a bone (2) comprises the steps of: preparing the bone (2) in order to be accessible to an osteotomic instrument; predefining an osteotomic geometry on the bone (2); and applying the osteotomic instrument to the bone (2) thereby cutting the bone (2) along the osteotomic geometry and generating a cut surface (21) to the bone (2). The method further comprises delivering a laser beam to the cut surface (21) of the bone (2) such that the cut surface (21) of the bone (2) is ablated. The method according to the invention allows to improve healing of a bone at its cut surface after being cut by the osteotomic instrument.

13 Claims, 5 Drawing Sheets

(51) Int. Cl.
  *A61B 17/56* (2006.01)
  *A61B 17/16* (2006.01)
  *A61B 18/22* (2006.01)

(52) U.S. Cl.
  CPC ............... *A61B 2017/564* (2013.01); *A61B 2018/00035* (2013.01); *A61B 2018/00565* (2013.01); *A61B 2018/00577* (2013.01); *A61B 2018/00601* (2013.01); *A61B 2018/00642* (2013.01); *A61B 2018/00809* (2013.01); *A61B 2018/00904* (2013.01); *A61B 2018/20359* (2017.05); *A61B 2018/20361* (2017.05); *A61B 2018/2211* (2013.01)

(56) References Cited

U.S. PATENT DOCUMENTS

| | | | |
|---|---|---|---|
| 7,346,417 B2 | 3/2008 | Luth | |
| 2002/0107522 A1 | 8/2002 | Picard | |
| 2010/0082032 A1* | 4/2010 | Berna | A61C 8/0089 606/79 |
| 2012/0245589 A1* | 9/2012 | Fisher | A61B 17/157 606/87 |

FOREIGN PATENT DOCUMENTS

| | | |
|---|---|---|
| EP | 2749234 A1 | 7/2014 |
| EP | 2821023 A1 | 1/2015 |

OTHER PUBLICATIONS

Written Opinion of the International Searching Authority for International Application No. PCT/EP2016/070988 dated Nov. 8, 2016 (7 Sheets).

International Search Report for International Application No. PCT/EP2016/070988 dated Nov. 8, 2016 (6 Sheets).

* cited by examiner

BONE CUT TREATMENT

TECHNICAL FIELD

The present invention relates to a device for treating a cut surface of a bone, a method of manufacturing such a device, a method of cutting a bone, a method of preparing an osteotomy and a method of in vitro cutting a bone.

Such cutting methods comprising the steps of preparing the bone in order to be accessible to an osteotomic instrument, predefining an osteotomic geometry on the bone, and applying the osteotomic instrument to the bone thereby cutting the bone along the osteotomic geometry and generating a cut surface to the bone can be used for cutting bones in a broad variety of medical applications.

BACKGROUND ART

In many medical applications human or animal bones are cut or drilled for many varying purposes. For example, for correcting the shape of a bone it is known to apply one or plural cuts to a bone and to reshape the bone along the cuts. Or, for replacing a tooth it is common practice to drill a hole in the jaw bone and to provide an implant into the drilled hole as an artificial tooth root.

Before cutting a bone usually the bone is analyzed and an osteotomic geometry is defined on the bone. When defining the osteotomic geometry the target of the cutting process is to consider as well as the given structure of the bone. Also, before a cut is applied the bone typically is prepared such as made accessible and the like. Once the osteotomic geometry is defined and the bone is prepared an appropriate osteotomic instrument is chosen for the intervention. Thereby, many different osteotomic instruments are known and commonly used today such as electric or pneumatic saws, drills or the like.

For example, for applying cylindrical or conical holes into a bone such as, e.g., for setting a dental implant often mechanical drills are used. Or for applying cuts along a line a variety of saws as well as piezoelectric osteotomes are known. Since there is a long and broad experience in using such instruments its use can be comparably efficient and is preferred by many surgeons.

In most medical applications involving cutting of bones healing of the bone is important for the success of the overall process. Thereby, usually ossification is a crucial part of the healing of the bone. For example, for setting an implant into a jawbone the implant has to become ingrown into the jawbone by ossification of the bone structure at the cut surface of the drill around the implant. Or, when reshaping a bone the bone pieces have to grow together including ossification of the cut surfaces neighboring each other.

However, after applying an osteotomic instrument as mentioned above the cut surface healing also includes recovery from the cutting process since, typically, the bone structure is impaired at the cut surface. Such recovery precedes the starting of essential ossification. Thus, the targeted ossification usually is delayed by the recovery of the cut surface. In many applications this delay is comparably cumbersome since, e.g., measures have to be taken to protect the cut surfaces. Also, often the medical application or treatment is slowed or completely interrupted by the recovery of the cut surface of the bone which can make the overall process essentially less efficient.

Therefore, there is a need for a method or a device allowing to improve healing of a bone at its cut surface after being cut by an osteotomic instrument.

DISCLOSURE OF THE INVENTION

According to the present disclosure this need is settled by a device as it is defined in the following, by a method of preparing an osteotomy as it is defined in the following, by a method of manufacturing such a device as it is defined in the following, particularly by a method of cutting a bone as it is defined in the following and by a method of in vitro cutting a bone as it is defined in the following.

More particular, the mentioned need existing in the prior art can be settled in accordance with the invention by a method of cutting a bone comprising the steps of: Preparing the bone in order to be accessible to an osteotomic instrument, predefining an osteotomic geometry on the bone, and applying the osteotomic instrument to the bone, thereby, cutting the bone along the osteotomic geometry and generating a cut surface to the bone. The method of cutting a bone particularly further comprises the step of delivering a laser beam to the cut surface of the bone such that the cut surface of the bone is ablated. The method of cutting a bone can also be applied in vitro as an embodiment of the invention.

In the context of the present disclosure, a osteotomic instrument can be, for example, a drill, a piezoelectric osteotome or a saw such as an oscillating saw. The term "cut surface" can relate to any open surface generated to the bone by a cutting process. For example, when a bone is cut apart the cut surface is the generated surface where the bone pieces face each other. Or, for example, when a hole is drilled into the bone, the cut surface can be the inner surface of the drill hole.

The term "bone" as used herein refers to natural human or animal bones as well as to artificial bones or bone replacements.

The term "osteotomic geometry" as used herein relates to any geometry defined to the bone for specifying the cut applied to the bone. Such osteotomic geometry can be, for example, a straight or curved line along which the bone is to be cut, a hole which is to be drilled into the bone or a more complex geometry defining a target fashion of intervening the bone. The osteotomic geometry typically is predefined in a preoperative planning step. It can be predefined based on data gathered of the bone such as, e.g., computer tomography data. The osteotomic geometry can be predefined by means of a computer or directly on the bone or the like.

The principal generally underlying the cutting of bones by means of conventional osteotomic instruments is essentially the same for all different types of instruments. This is, the respective instrument puts mechanical stress onto the bone surface until a surface hardness is exceeded and the instrument breaks into the bone.

Thereby, induced by the applied mechanical forces a structure of the bone is modified at the cut surface generated by the osteotomic instrument. In particular, during the mechanical cutting process a flattened tissue structure or smear layer is generated at the cut surface of the bone (see FIG. 8). Beyond others this smear layer is the consequence of debris being pressed or squeezed into the bone structure by the osteotomic instrument. The flattened down and closed cut surface can have tension cracks and even scratches from the osteotomic instrument. Removal of the debris from the bone structure and recovery of the bone structure can take some time such as a couple of days or the like. Such delay of recovery hinders the further healing processes of the bone such as, in particular, ossification.

By ablating the cut surface by means of a laser beam the smear layer generated by the osteotomic instrument can be removed (see FIG. 9). In particular, when ablating bone tissue by means of the laser beam the debris generated travels away from the bone at comparably high velocities such as, e.g. at about 2'000 m/s. Therefore, from the perspective of the bone the ablation by the laser beam can be referred to as debris free or the complete ablation can be referred to as cold (photo) ablation. Thus, the laser beam allows for precisely ablating the smear layer and to regenerate the natural structure of the bone tissue at the cut surface. Such natural open structure of the bone can be highly beneficial for its healing which is crucial in many surgical applications. For example, such regenerated structure allows for minimizing or even eliminating recovery of the bone before substantial ossification can start at the cutting surface. Thus, the method of cutting a bone according to the invention allows improving healing of the bone at its cut surface after being cut by the osteotomic instrument.

Such improved healing of the bone can additionally be beneficial, e.g., when an implant is involved which is to be grown together with the bone. Also, it is known that when conventionally growing an implant to a bone a certain percentage of implants such as, e.g., 5%, of the implants is rejected. In such a situation of rejection the implant can be removed and after the bone being ablated in accordance with the method of cutting a bone the implant can be repositioned. The subsequent healing can be essentially better and, in particular, rejection of the implant can be reversed.

Preferably, delivering the laser beam to the cut surface of the bone comprises removing a layer of bone tissue at the cut surface of the bone. By removing a complete layer of bone tissue at the cut surface a regeneration of the bone at the complete cut surface can be achieved. Thereby, the layer of the bone tissue preferably has a thickness in a range of about one to about eight micrometer or, particularly, in a range of about two to about five micrometer. Such layer can, e.g., be sufficient to remove the smear layer mentioned above or any other cut surface damage of the bone.

Preferably, delivering the laser beam to the cut surface of the bone comprises the laser beam applying lines of adjacent spots. The spots can have an essentially circular shape. By ablating the cut surface with spots induced by the laser beam it can be prevented or at least be minimized that essential heat is transferred from contact area where the laser beam hits the bone to other parts of the bone. More particular, the single spots can be cooled after being generated and before the next spot is provided. Like this collateral damages of the bone by heat can be prevented or minimized.

Thereby, delivering the laser beam to the cut surface of the bone preferably comprises applying further lines of further adjacent spots wherein the further adjacent spots are offset and between the adjacent spots. By generating such a grid of spots the complete cut surface can be ablated. Furthermore, since the spots of different rows are offset it can be prevented that the laser beam hits the same spot at an overlap with an adjacent spot.

The spots preferably have a diameter in a range of about four hundred micrometer to about five millimeter or in a range of about four hundred micrometer to about one millimeter or in a range of about four hundred micrometer to about six hundred micrometer or, particularly, a diameter of about five hundred micrometer. Spots of such a dimension can be precisely and efficiently created by laser devices.

Preferably, the laser beam is a pulsed laser beam. The pulses of such a laser beam can be sub-microsecond pulses. The laser beam preferably is generated by a solid-state Erbium laser device such as a solid-state Erbium laser source described below Such devices and pulsed laser beams allow for a precise and efficient ablation of the cut surface with no or minimal collateral damages on the bone structure.

Preferably, the laser beam has a wavelength in a range of about two thousand nine hundred nanometer to about three thousand nanometer or, particularly, a wavelength of about two thousand nine hundred and forty nanometer. Such wavelength can particularly be suitable for being delivered to bone tissue. Selection of the laser and adjustment to correct properties can be crucial for efficiently removing bone tissue at a comparably low depth. Thus, an efficient ablation of the bone tissue at the cut surface can be provided.

Preferably, delivering the laser beam to the cut surface of the bone comprises cooling and hydrating the bone where the laser beam is applied. Such cooling and hydrating may be performed with a nozzle array wherein multi-fluid nozzles can be particularly efficient. The cooling fluid can be a sterile sodium chloride. It allows for minimizing heat transfer from the laser beam—bone tissue contact area to other sections of the bone. Thus, collateral damages of the bone tissue can be prevented or minimized.

The present invention further deals with a device for treating a cut surface of a bone. The device comprises a laser source for generating a laser beam and a support carrying the laser source. The support of the device has a mounting structure adapted to be connected to the bone such that the laser source is in a predefined position and orientation to the cut surface of the bone.

The term "predefined position and orientation" in connection with the device can relate to any predefined position and predefined orientation allowing the laser source to deliver a suitable beam to the bone in order to ablate its cut surface. Thereby, the position can be predefined in vicinity of the cut surface of the bone such that a laser beam generated by the laser source can unhinderedly reach the cut surface. The orientation of the laser source can be predefined such that a laser beam generated by the laser source can directly reach the cut surface at a preferred angle. Such predefined angle can particularly be an essentially right angle.

The term "adapted to be connected to the bone" in connection with the mounting structure relates to the mounting structure being featured, embodied or designed appropriately. Thereby, the mounting structure can be embodied in various differing ways depending on the situation and the structure of the bone. For example, it can have clipping or clamping means allowing to be releasably but firmly mounted to the bone. Or it can have a hole, which can additionally be equipped with a thread, for receiving a screw to be screwed to the bone. Or it can comprise a belt or a filament which allows to tie the device to the bone. Or it can be equipped with a spike or an adhesive for being attached to the bone. The mounting structure can also have other such connection elements or it can have a combination of the before mentioned connection elements.

Besides the connection elements the mounting structure can have positioning elements such as legs or the like to properly position the laser source in relation to the bone. Additionally, the mounting structure can have a surface shaped in accordance with the location on the bone where the laser device is to be connected. Such surface may help to stabilize the device in relation to the bone.

The device according to the invention allows for implementing the method of cutting a bone described above in an efficient and convenient manner. Thereby, the effects and advantages described above in connection with the method of cutting a bone and its preferred embodiments can efficiently be realized and achieved.

Preferably, the device comprises a drive unit adapted to move the laser beam along the cut surface of the bone. With such a drive unit the laser beam can automatically or semi-automatically be moved over the cut surface of the bone. For example, the drive unit can be programmable such that in a preoperative planning step it can be adjusted to ablate the cut surface. The drive unit allows for increasing efficiency and accuracy when ablating the cut surface of the bone.

Thereby, the drive unit preferably comprises a laser source positioner adapted to move the laser source in relation to the bone when the device is connected to the bone by the support. With such a laser source positioner or navigation system the laser beam generated by the laser source can be guided along the cut surface of the bone by moving the laser source or parts thereof. Alternatively or in addition thereto, the drive unit preferably comprises an adjustable optics adapted to move a direction in which the device provides the laser beam. Such optics enables for precisely and efficiently delivering the laser beam generated by the laser source to cut surface of the bone for ablating it. Thereby, in one embodiment the adjustable optics preferably comprises a mirror deflecting the laser beam provided by the laser source, wherein the mirror can be rotated around an axis such that the laser beam can be radially provided around 360°. Such a mirror allows for efficiently treating the inner surface of a drill hole being the cut surface of the drill hole.

Preferably, the device comprises a depth detecting unit adapted to detect a depth of an ablation applied to the cut surface of the bone by the device. Such a device allows for precisely ablating a layer of bone tissue of a specific thickness. Thereby, variations in the nature of the bone tissue over the cut surface can be considered. Also, such depth detecting unit allows for providing a comparably flat surface and an unevenness of the cut surface can be eliminated. Particularly when being combined with a drive as described above such depth detecting unit allows for a very precise and efficient ablation of the cut surface of the bone. For example, the depth detecting unit can continuously provide information about the depth of the ablated bone tissue to a central control unit which adjusts the drive in response thereto.

Preferably, the device comprises an auto focusing arrangement to automatically adjust a focus of the laser beam in relation to the cut surface of the bone. Such focusing arrangement allows for continuously adapting the focus with advancing ablation. In an advantageous embodiment the auto focusing arrangement is combined with the depth detecting unit mentioned above. Thereby, the auto-focusing arrangement preferably is adapted to adjust the focus of the laser beam in accordance with the depth detected by the depth detecting unit. In this way, the focal point of the laser beam can automatically be adjusted in order to ensure that a predefined laser beam intensity hits the cut surface of the bone. Thereby, the focus can be continuously adjusted in accordance with the respective depth of the ablated bone tissue.

Preferably, the laser source is a solid-state Erbium laser source or, particularly, a solid-state Erbium-doped Yttrium Aluminium Garnet laser source. Such a laser source can be particularly suitable for ablating bone or other human or animal hard tissue.

The device can further comprise a debris extraction unit adapted to remove debris generated by the laser beam hitting the cut surface of the bone. Such debris extraction can help to keep the cut surface and the room around it clean.

Another aspect of the invention relates to a method of preparing an osteotomy (preparation method) comprising the steps of: Obtaining data about a bone; predefining an osteotomic geometry on the bone; choosing an osteotomic instrument suitable for cutting the bone along the osteotomic geometry and for thereby generating a cut surface to the bone; and allocating a timeframe and defining an environment for preparing the bone in order to be accessible to the osteotomic instrument and for applying the osteotomic instrument to the bone thereby cutting the bone along the osteotomic geometry and generating a cut surface to the bone. The preparation method further comprises the steps of: Allocating a further timeframe and defining the environment for delivering a laser beam to the cut surface of the bone after the cut surface is generated to the bone; and arranging the environment in accordance with its definition in the allocated time frame.

The term "timeframe", as used in connection with the preparation method, can relate to a duration and a sequence in which one or plural specific steps are performed. By allocating a timeframe the respective step(s) of the process or method can be ordered in the context of the osteotomy or surgical procedure. Thus allocating a timeframe with the preparation method allows for planning and efficiently performing the associated step during later surgery or osteotomy.

The term "environment", as used in connection with the preparation method, can relate to anything which is necessary in the planned intervention. It can, for example, include the physical environment such as the room and furniture involved, the personnel required, the instruments and tools to be used and the positioning of anything involved.

Thus, by allocating a timeframe and defining an environment the related step(s) or process can be planned and organized. This allows for efficiently performing this step(s) or process in real once the surgery or osteotomy is performed. All the steps of preparing the osteotomy in accordance with the invention are performed before any intervention to the bone or the patient at all. Thereby, the preparation method is performed without any surgical action or the like. Moreover, only after the environment is prepared in accordance with the preparation method the workspace of the surgeon is ready.

The method of preparing an osteotomy or preparation method can be part of a preoperative planning process. In particular, it can be performed in order to efficiently prepare an operation such that a later intervention or surgical procedure can be beneficially implemented. In particular, the preparation method can allow for efficiently applying an embodiment of the method of cutting a bone described above. More specifically by allocating a further timeframe and defining the environment for delivering a laser beam to the cut surface of the bone after the cut surface is generated to the bone and by arranging the environment in accordance with its definition in the allocated time frame, the method of cutting a bone described above can be organized and efficiently applied. Thereby, the preparation method allows for efficiently achieving the effects and benefits described above in connection with the method of cutting a bone.

Preferably, the step of obtaining the data about the bone comprises analyzing the bone with computer tomography. Such computer tomography analysis allows for precisely defining the osteotomic geometry prior to any surgical intervention, e.g., on a computer or the like. This allows for efficiently cutting the bone at a later stage within the surgical intervention.

In the following, features of preferred embodiments of the method of preparing an osteotomy are listed which enable implementing corresponding preferred embodiments of the method of cutting a bone described above. Thereby, the effects and benefits described above in connection with the corresponding embodiments of the method of cutting the bone can be correspondingly achieved or supported.

Preferably, the further timeframe is allocated and the environment is defined in accordance with delivering of the laser beam to the cut surface of the bone comprising ablating the cut surface of the bone.

Preferably, the further timeframe is allocated and the environment is defined in accordance with delivering the laser beam to the cut surface of the bone comprising removing a layer of bone tissue at the cut surface of the bone.

Preferably, the further timeframe is allocated and the environment is defined in accordance with the layer of the bone tissue having a thickness in a range of about one to about eight micrometer or, particularly, in a range of about two to about five micrometer.

Preferably, the further timeframe is allocated and the environment is defined in accordance with delivering the laser beam to the cut surface of the bone comprising the laser beam applying lines of adjacent spots.

Thereby, the further timeframe preferably is allocated and the environment preferably is defined in accordance with delivering the laser beam to the cut surface of the bone comprising applying further lines of further adjacent spots wherein the further adjacent spots are offset and between the adjacent spots.

Thereby, the further timeframe preferably is allocated and the environment preferably is defined in accordance with the spots having a diameter in a range of about four hundred micrometer to about five millimeter or in a range of about four hundred micrometer to about one millimeter or in a range of about four hundred micrometer to about six hundred micrometer or, particularly, a diameter of about five hundred micrometer.

Preferably, the further timeframe is allocated and the environment is defined in accordance with the laser beam being a pulsed laser beam. The pulses applied by such a laser can be sub-millisecond pulses.

Preferably, the further timeframe is allocated and the environment is defined in accordance with the laser beam being generated by a solid-state Erbium laser device or, particularly, by a solid-state Erbium-doped Yttrium Aluminium Garnet laser device.

Thereby, the further timeframe preferably is allocated and the environment preferably is defined in accordance with the laser beam having a wavelength in a range of about two thousand nine hundred nanometer to about three thousand nanometer and particularly with a wavelength of about two thousand nine hundred and forty nanometer.

Preferably, the further timeframe is allocated and the environment is defined in accordance with delivering the laser beam to the cut surface of the bone comprising cooling and hydrating the bone where the laser beam is applied. Such cooling and hydrating may be performed with sterile sodium chloride.

A further other aspect of the invention relates to a method of manufacturing a device for treating a cut surface of a bone (manufacturing method). This method comprises the steps of: obtaining bone information about the bone and its cut surface; based on the gathered bone information, adapting a mounting structure of a support to be suitable to being connected to the bone such that the laser source is in a predefined position and orientation to the cut surface of the bone; equipping the support with a laser source for generating a laser beam such that the support carries the laser source; and equipping the device with the support.

With such a method, the laser device can be realized in an efficient manner. The manufacturing method can also be completed or extended by respective steps to embody the device in accordance with the preferred embodiments described above. Thereby, the effect and benefits of the laser device according to the invention and its preferred embodiments can efficiently be realized.

BRIEF DESCRIPTION OF THE DRAWINGS

The device for treating a cut surface of a bone according to the invention, the method of cutting a bone according to the invention and the method of preparing an osteotomy according to the invention are described in more detail herein below by way of exemplary embodiments and with reference to the attached schematic drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly.

Likewise, descriptions of movement along and around various axes includes various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
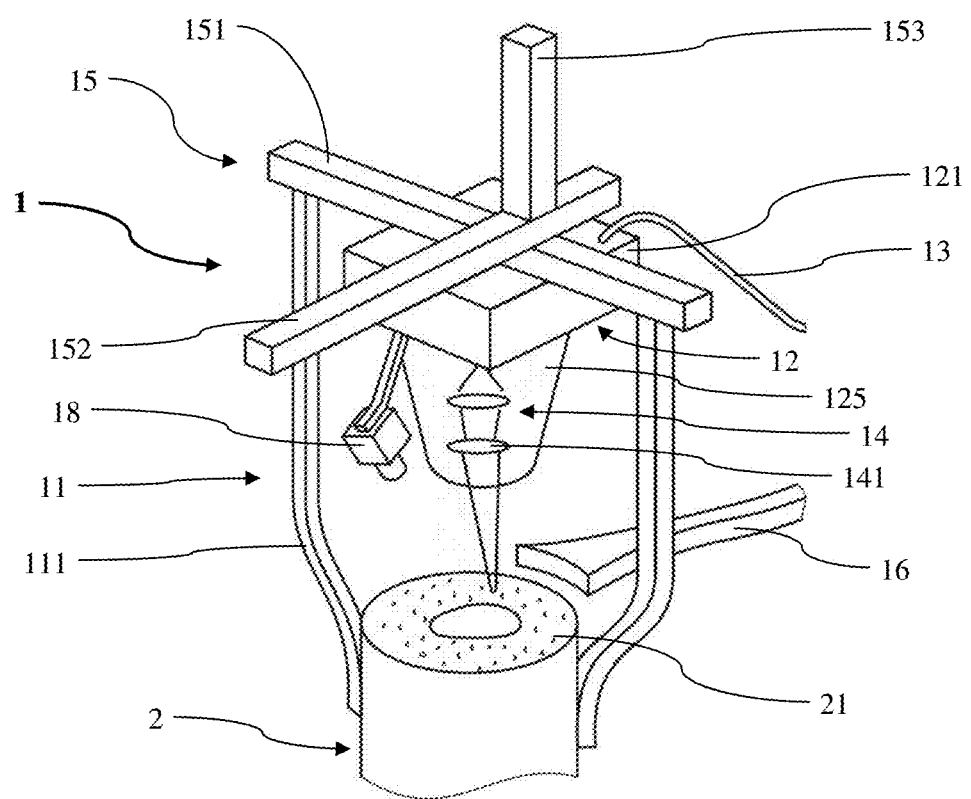
FIG. 1 shows a perspective view of a portion of a first embodiment of a device according to the invention.

FIG. 1 shows a first embodiment of the device 1 for treating a cut surface of a bone according to the invention. The device 1 comprises a laser source 12, a drive unit 15, an autofocusing arrangement 14, a debris extraction unit 16, a support 11 and a media wiring 13. The support 11 has two legs 111 as mounting structure. The legs 111 are at one longitudinal end connected to the drive unit 15. At the opposite longitudinal end the legs 111 are adapted to be connected to a bone 2. In particular, the legs 111 are shaped to clamp the bone 2 in between each other. The bone 2 has earlier been cut by an appropriate cutting instrument such as a saw and presents a cut surface 21 where the cutting instrument has been applied. The legs 111 are arranged such that the laser source 12 and particularly a laser head 121 thereof is in precisely positioned and oriented with respect to the cut surface 21 of the bone 2.

The laser source 12 has the laser head 121 which is directly attached to the drive unit 15 and a nozzle body 125 connected to the laser head 121 and directed towards the cut surface 21 of the bone 2. In FIG. 1 the nozzle body 125 is drawn partially transparent such that lenses 141 of the autofocusing arrangement 14 which are arranged inside the nozzle body 125 are visible. The lenses 141 of the autofocusing arrangement 14 focus a laser beam generated by the laser source 12 and directed to the cut surface 21 of the bone 2 such that its intensity is adapted to ablate bone tissue at the cut surface 21.

The debris extraction unit 16 has a nose positioned close to the cut surface 21 of the bone 2. Through its nose the debris extraction unit 16 sucks debris generated by the ablation of the bone tissue by the laser beam from the cut surface 21 of the bone 2.

The drive unit 15 comprises three perpendicularly arranged rails. More particularly, these rails consist of an x-rail 151, a y-rail 152 and a z-rail 153.

The device 1 further comprises a camera 18 which is positioned below the laser head 121 of the laser source 12. It is directed to the cut surface 21 of the bone 2 and particularly to an area thereof where the laser beam hits the cut surface 21. By means of the camera the ablation process can be monitored and evaluated. It can be an infrared camera suitable for measuring the temperature at the laser beam—bone tissue contact area.

Figure 2:
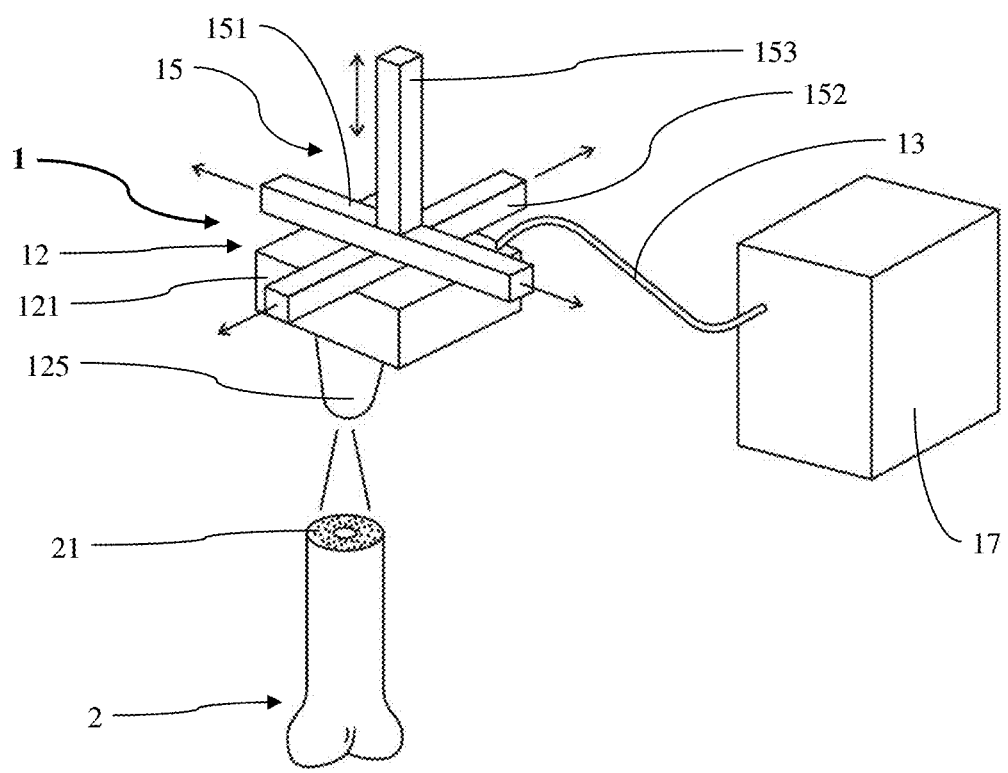
FIG. 2 shows a perspective view of a further portion of the device of FIG. 1.

In FIG. 2 the device 1 is shown in another view in which an electronic unit 17 of the device 1 is visible. The electronic unit 17 is connected to the laser head 121 of the laser source 12 via the media wiring 13. As indicated by the arrows shown in FIG. 2, the laser head 121 is movable by means of a motor of the drive unit 15 along the x-rail 151 of the drive unit 15 in an x-direction, along the y-rail 152 of the drive unit 15 in a y-direction perpendicular to the x-direction and along the z-rail 153 of the drive unit 15 in a z-direction perpendicular to the x-direction and to the y-direction. Like this, the drive unit 15 can precisely position the laser head 121 of the laser source 12 relative to the cut surface 21 of the bone 2 in all three dimensions.

Figure 3:
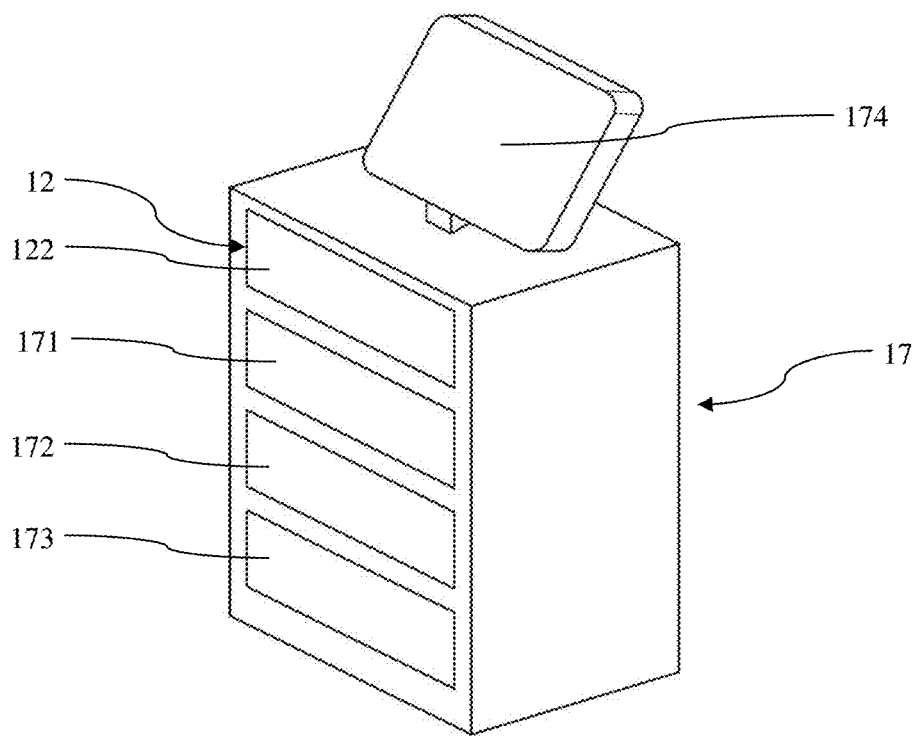
FIG. 3 shows a perspective view of an electronic unit of the device of FIG. 1.

FIG. 3 shows the electronic unit 17 of the device 1 in more detail. It comprises a gas and liquid control 171, a depth control 172, a processing unit 173 and a display 174. Furthermore, it is equipped with a solid-state Erbium-doped Yttrium Aluminium Garnet (Er:YAG) laser 122 of the laser source 12.

Figure 4:
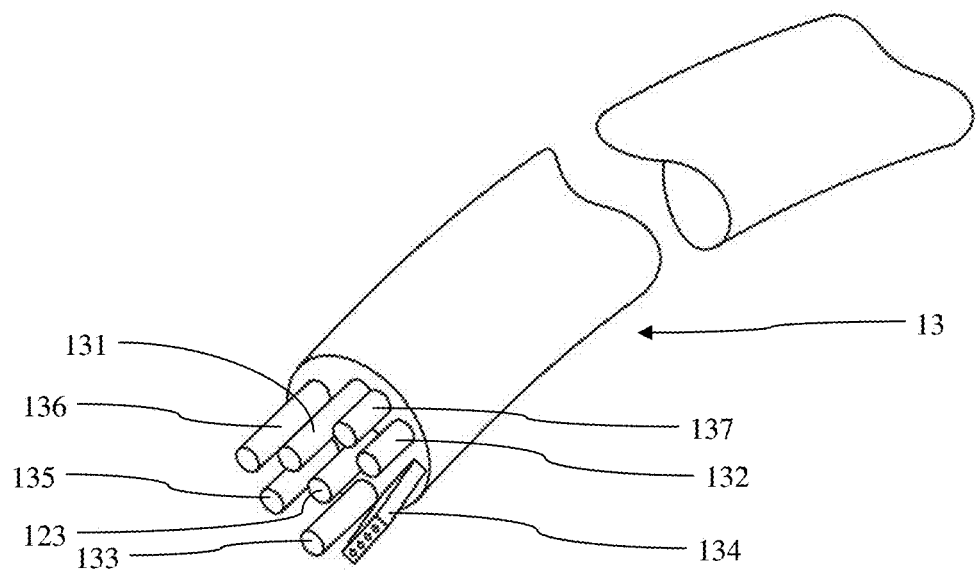
FIG. 4 shows a perspective view of a media wiring of the device of FIG. 1.

As shown in FIG. 4 the media wiring 13 comprises a forward cooling media tube 131, a backward cooling media tube 132, a gas tube 133, power supply cables 134, a depth control optical fiber 135, an ablation optical fiber 136 and a controller cable 137. It further houses an ablation optical fiber 123 of the laser source 12.

The power supply cables 134 are connected to all power consumers remote from the electronic unit 17. Thereby, the power consumers such as, in particular, the motor of the drive unit 15, the camera 18, the debris extraction unit 16 and the autofocusing arrangement 14 are supplied with electric energy via the power supply cables 134 of the media wiring 13.

The forward cooling media tube 131 and the backward cooling media tube 132 are connected to a cooling entity. The cooling medium can be any liquid or other medium such as a sole suitable for cooling the attached components such as the laser head 121 or the like. More particularly, in the forward cooling media tube 131 the cooling medium is provided from a cooling medium reservoir to the cooling entity and in the backward cooling media tube 132 the heated cooling medium is provided back after circulating through the cooling entity.

The gas tube 133 and the liquid tube 136 are connected to the nozzle body 125 of the laser head 121 of the laser source 12. The nozzle body 125 comprises plural two-fluid nozzles directed to the laser beam—bone tissue contact area. By the two-fluid nozzles the liquid provided by the liquid tube 136 such as, e.g., sterile sodium chloride or distilled water which can be enriched with an antiseptic substance, and the gas provided by the gas tube 133 are mixed at an elevated pressure in order to generate a spray. During ablation of the bone tissue the two-fluid nozzles direct sprays to the laser beam—bone tissue contact area for cooling and thereby minimizing heat transfer in the bone tissue. For example, the two-fluid nozzles can deliver the sterile sodium chloride to the cut surface 21 at a flow rate of about 8 to 10 ml/min under a pressure of about 3 bar. The liquid is then removed from the cut surface 21 of the bone together with the debris by the debris extraction unit 16.

The controller cable 137 is connected to the processing unit 173 and the controllable components of the device 1 such as the motor of the drive unit 15, the camera 18, the autofocusing arrangement 14, the two-fluid nozzles of the nozzle body 125 and the like. Through the controller cable 137 the processing unit 173 communicates with the mentioned controllable components. For example, the processing unit automatically adjusts the orientation of the lenses 141 of the autofocusing unit 14 considering the depth of the ablation of the bone tissue on the cut surface 21 of the bone 2.

Figure 5:
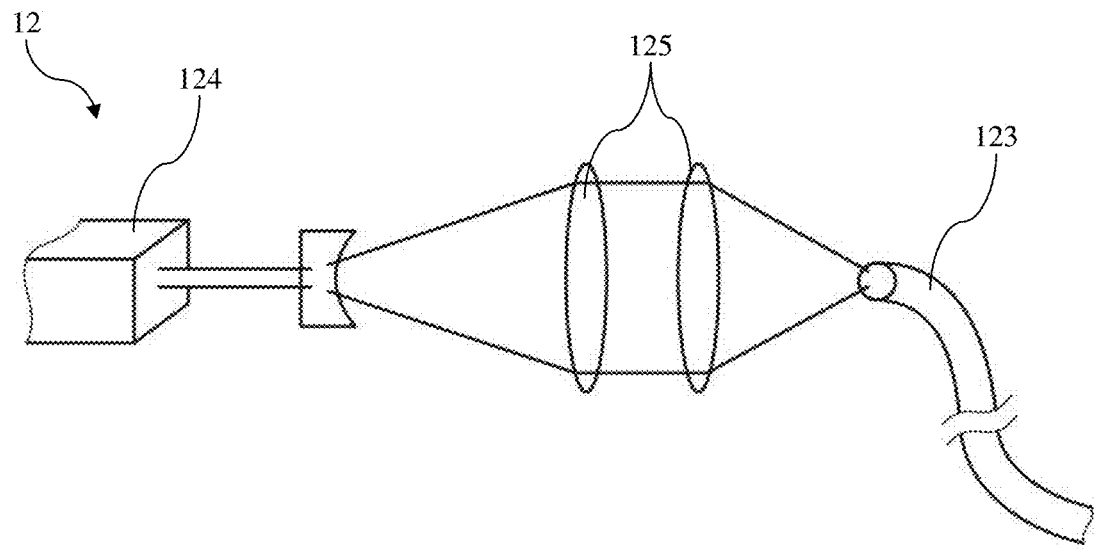
FIG. 5 shows a detail of a laser source of the device of FIG. 1.

Through the ablation optical fiber 123 a laser beam is provided from the Er:YAG laser 122 passing the autofocusing arrangement 14 out of the nozzle body 125. For this, the laser beam is introduced into the ablation optical fiber 123 as shown in FIG. 5. In particular, the Er:YAG laser 122 of the laser source 12 has a beam generator 124. An initial laser beam exits the beam generator 124 and is directed by focusing lenses 125 of the laser source 12 into the ablation optical fiber 123. There, it travels to the laser head 121 and exits the laser source 12 through the nozzle body 125. Thereby, the laser beam is focused by the autofocusing arrangement 14 to the cut surface 21 of the bone 2. By the autofocusing arrangement 14, the intensity of the laser beam at the cut surface 21 can precisely be adjusted. This allows for efficiently ablating the bone tissue at the cut surface 21.

Figure 6:
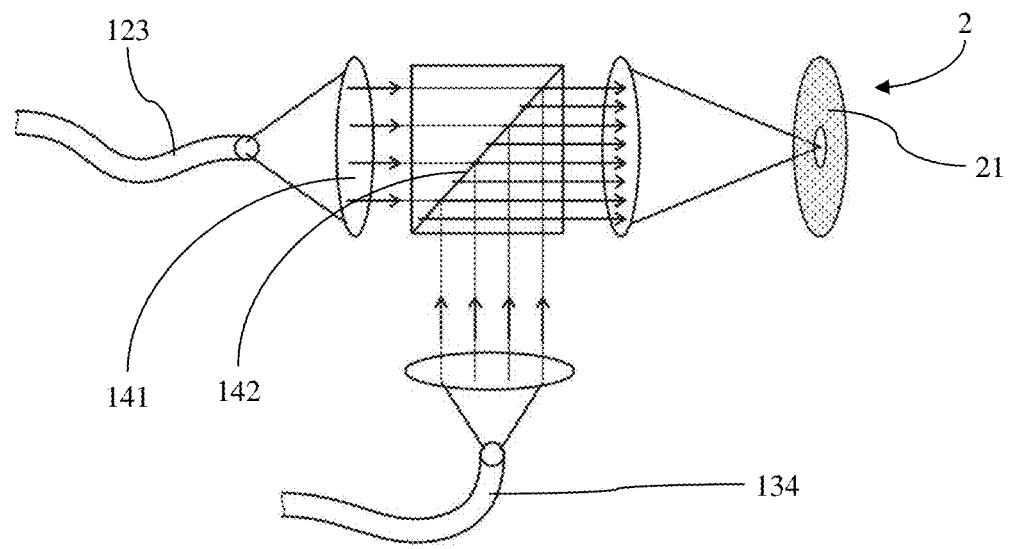
FIG. 6 shows a detail of a laser beam mixing arrangement of the device of FIG. 1.

Similarly as the laser beam for ablating the bone tissue a second laser beam is provided through the depth control optical fiber 135. This second laser beam is for detecting the depth of the ablation process on the bone 2. As shown in FIG. 6 the second laser beam is mixed with the laser beam within the autofocusing arrangement 14. In particular, the autofocusing arrangement 14 comprises a dichromatic mirror 142. The laser beam aligned by a first lens 141 passes the dichromatic mirror 142 from its backside. The second laser beam aligned by a second lens 141 is provided perpendicular to the laser beam on the front side of the dichromatic mirror 142. There it is reflected by the dichromatic mirror 142 in the same direction as the laser beam. The laser beam together with the second laser beam are focused by a third lens 141 and directed to the cut surface 21 of the bone 2.

In use the device 1 can be applied in an embodiment of a method of cutting the bone 2 according to the invention. Before the device 1 is used the bone 2 is prepared in order to be accessible to an osteotomic instrument. For preparing the bone and the complete osteotomy an embodiment of a method of preparing an osteotomy according to the invention can be applied preoperatively. Thereby, data about the bone 2 is obtained by computer tomography. The data is analysed and on the computer tomography image an osteotomic line is defined on the bone 2 as osteotomic geometry. Then a saw is chosen as osteotomic instrument suitable for cutting the bone 2 along the osteotomic line and for, thereby, generating the cut surface 21 to the bone 2. In the preoperative planning a timeframe is allocated and an environment defined in which the bone 2 is prepared in order to be accessible to the saw and in which the saw is applied to the bone 2 thereby cutting the bone 2 along the osteotomic geometry and generating the cut surface 21 to the bone 2. The preoperative planning further includes that a further timeframe is allocated and that the environment is further defined for delivering a laser beam to the cut surface 21 of the bone 2 after the cut surface 21 is generated to the bone 2. The environment is then arranged in accordance with its definition in the allocated time frame.

After the preoperative planning is finished the method of cutting the bone 2 is continued by applying the saw to the bone 2, thereby, cutting the bone 2 along the osteotomic line and generating the cut surface 21 to the bone 2 as shown in the drawings. After the bone is cut the device 1 is attached to the bone 2 as shown in FIG. 1. Then, a laser beam is delivered to the cut surface 21 such that the cut surface 21 is ablated.

For ablating the cut surface 21, the processing unit 173 controls the drive unit 15 such that it moves the laser head 121 of the laser source 12 together with its nozzle body 125 over the cut surface 21. Thereby, the sub-microsecond pulsed laser beam generated by the laser source 12 of the device 1 creates lines of adjacent circular spots and further lines of further adjacent circular spots. The further adjacent spots are offset and between the adjacent spots. Like this a pattern of spots is created on the cut surface 21 covering the complete area of the cut surface 21. Moreover, since the spots and lines are created alternatingly the bone tissue has time to cool down which allows for minimizing collateral damages to the bone tissue.

In order to efficiently ablating the bone tissue at the cut surface 21, the laser beam generated by the laser source 12 is adjusted to have a wavelength in 2'940 nm. During delivery of the laser beam to the cut surface 21 of the bone 2 a sterile sodium chloride is sprayed to the cut surface 21 by the two-fluid nozzles in the nozzle body 125. Like this the cut surface 21 of the bone 2 is cooled and hydrated where the laser beam is applied.

During ablation the depth control 172 monitors and controls the depth of the ablated bone tissue. The laser beam is adjusted to the depth such that a regular layer of bone tissue is ablated from at the cut surface 21. In particular, a layer of bone tissue including a smear layer generated by the saw to the bone is removed.

Figure 7:
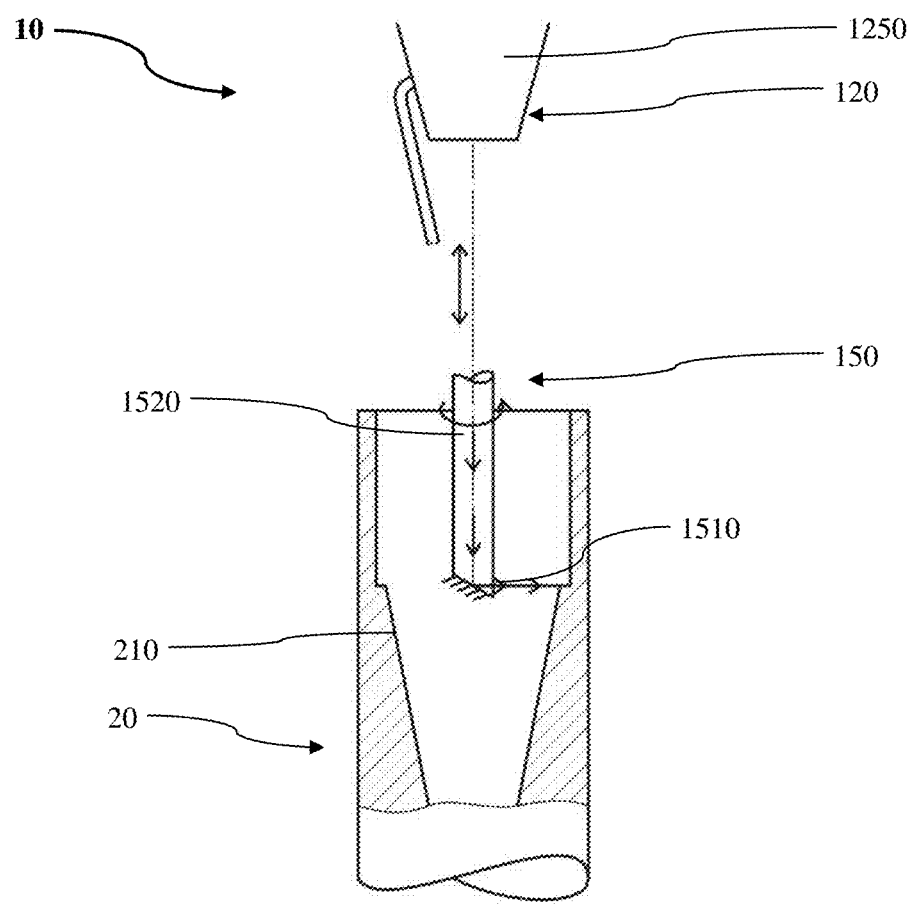
FIG. 7 shows a perspective view of a portion of a second embodiment of a device according to the invention.

FIG. 7 shows a second embodiment of a device 10 for treating a cut surface 210 of a bone 20 according to the invention. The bone 20, e.g., is a jaw bone or a femoral bone ready for artificial hip joint replacement or revision and the cut surface 210 is the interior surface of a drill hole generated in the jaw bone 20. The device 10 is similarly embodied as the device 1 shown in FIGS. 1 to 6 and described above. In contrast to the device 1 a drive unit 150 of the device 10 has a beam guide rod 1520 extending downwardly from a nozzle body 1250 of a laser source 120. At its lower end the beam guide rod 1520 is connected to a mirror 1510 of the drive unit 150. The beam guide rod 1520 is rotatable around its longitudinal axis by 360°. It is further movable along its longitudinal axis in relation to the nozzle body 120.

In use the device 10 is similarly prepared and applied as described above in connection with the device 1. The laser beam is delivered via the beam guide rod 1520 into the drill hole of the bone 20. At the end of the beam guide rod 1520 the laser beam is deflected by the mirror 1510 and directed towards the cut surface 210 of the bone 20. By the movable and rotatable beam guide rod 1520 the complete cut surface 210 of the bone 20 can efficiently be ablated.

Figure 8:
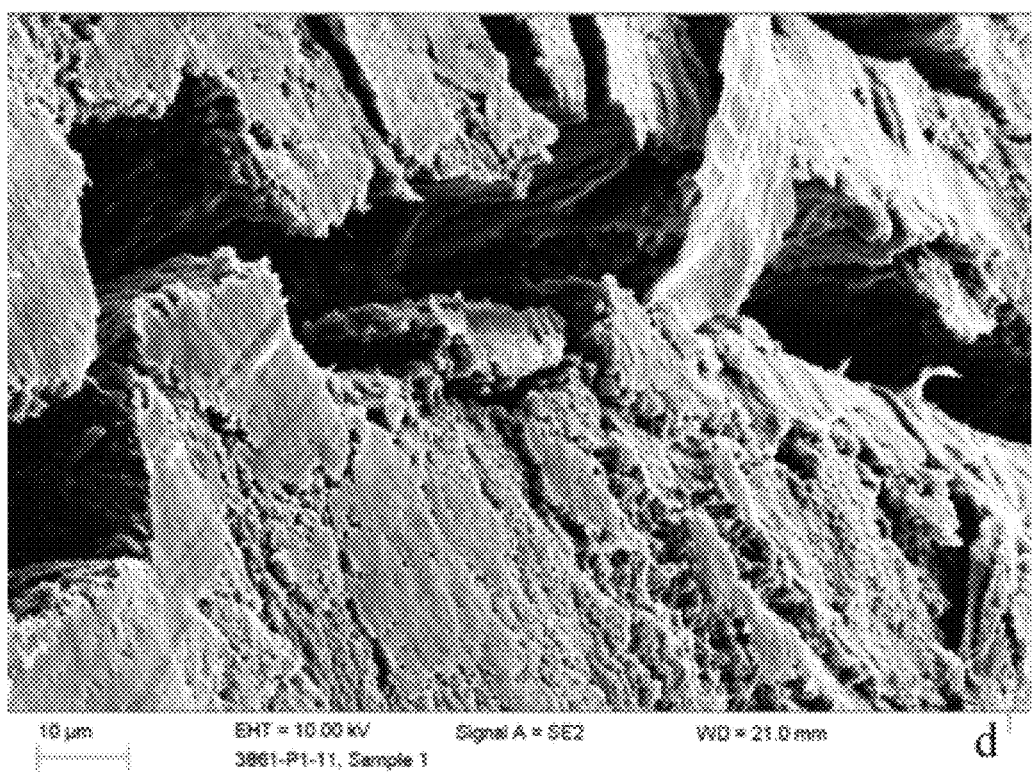
FIG. 8 shows a scanning electron microscopy image of a cut surface of a bone generated by a piezoelectric osteotome.

FIG. 8 shows a scanning electron microscopy image of a cut surface of a bone at a thousandfold enlargement. The cut surface is generated by a piezoelectric osteotome as intervention instrument. As can be seen, during the mechanical cutting process the bone tissue structure at the cut surface is flattened and a smear layer is generated. The flattened down and closed cut surface has tension cracks and scratches from the piezoelectric osteotome. In this status, the bone tissue has to recover before an essential ossification can start. Naturally such recovery takes some time such as a plurality of days or the like.

Figure 9:
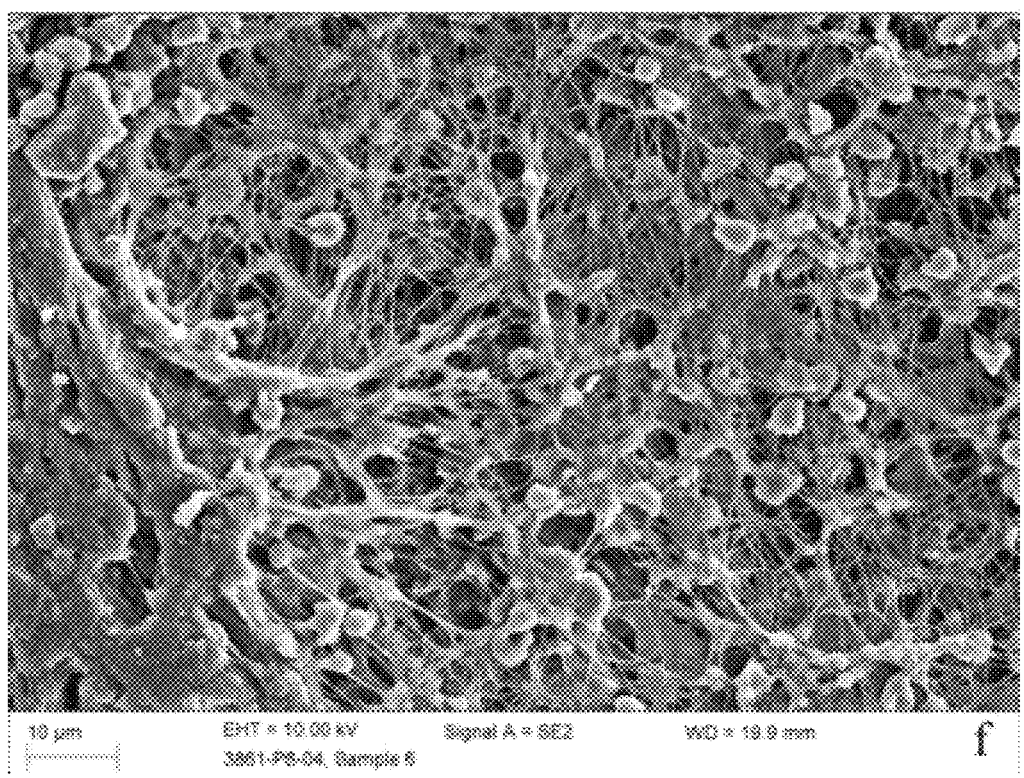
FIG. 9 shows a scanning electron microscopy image of a cut surface of a bone after being treated by a laser beam in accordance with the invention.

By ablating the cut surface by means of a laser beam the smear layer generated by the osteotomic instrument can be removed. In FIG. 9 a scanning electron microscopy image of the cut surface of the bone is shown at a thousandfold enlargement after being laser ablated. Therein, it can be seen that the bone tissue structure is open and comparably unimpaired since the smear layer is removed by the laser beam. Like this, the natural structure of the bone tissue at the cut surface can be regenerated comparably rapidly.

This description and the accompanying drawings that illustrate aspects and embodiments of the present invention should not be taken as limiting—the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The disclosure further comprises the following embodiments:

Embodiment 1 is a method of cutting a bone, comprising preparing the bone in order to be accessible to an osteotomic instrument,
predefining an osteotomic geometry on the bone, and
applying the osteotomic instrument to the bone thereby cutting the bone along the osteotomic geometry and generating a cut surface to the bone,
characterized by
delivering a laser beam to the cut surface of the bone such that the cut surface of the bone is ablated.

Embodiment 2 is a method according to embodiment 1, wherein delivering the laser beam to the cut surface of the bone comprises removing a layer of bone tissue at the cut surface of the bone.

Embodiment 3 is a method according to embodiment 2, wherein the layer of bone tissue has a thickness in a range of about one to about eight micrometer or, particularly, in a range of about two to about five micrometer.

Embodiment 4 is a method according any of the preceding embodiments, Method according to any one of embodiments 1 to 3, wherein delivering the laser beam to the cut surface of the bone comprises the laser beam applying lines of adjacent spots.

Embodiment 5 is a method according to embodiment 4, wherein delivering the laser beam to the cut surface of the bone comprises applying further lines of further adjacent spots wherein the further adjacent spots are offset and between the adjacent spots.

Embodiment 6 is a method according to embodiment 4 or 5, wherein the spots have a diameter in a range of about four hundred micrometer to about five millimeter or in a range of about four hundred micrometer to about one millimeter or in a range of about four hundred micrometer to about six hundred micrometer or, particularly, a diameter of about five hundred micrometer.

Embodiment 7 is a method according to any one of the preceding embodiments, wherein the laser beam is a pulsed laser beam.

Embodiment 8 is a method according to any one of the preceding embodiments, wherein the laser beam is generated by a solid-state Erbium laser device or, particularly, by a solid-state Erbium-doped Yttrium Aluminium Garnet laser device.

Embodiment 9 is a method according to any one of the preceding embodiments, wherein the laser beam has a wavelength in a range of about two thousand nine hundred nanometer to about three thousand nanometer or, particularly, a wavelength of about two thousand nine hundred and forty nanometer.

Embodiment 10 is a method according to any one of the preceding embodiments, wherein delivering the laser beam to the cut surface of the bone comprises cooling and hydrating the bone where the laser beam is applied.

Embodiment 11 is a device for treating a cut surface of a bone comprising
a laser source for generating a laser beam,
a support carrying the laser source and having a mounting structure adapted to be connected to the bone such that the laser source is in a predefined position and orientation to the cut surface of the bone.

Embodiment 12 is a device according to embodiment 11, comprising a drive unit adapted to move the laser beam along the cut surface of the bone.

Embodiment 13 is a device according to embodiment 12, wherein the drive unit comprises a laser source positioner adapted to move the laser source in relation to the bone when the device is connected to the bone by the support.

Embodiment 14 is a device according to embodiment 12 or 13, wherein the drive unit comprises an adjustable optics adapted to move a direction in which the device provides the laser beam.

Embodiment 15 is a device according to embodiment 14, wherein the adjustable optics comprise a mirror deflecting the laser beam provided by the laser source, wherein the mirror can be rotated around an axis such that the laser beam can be radially provided around 360°.

Embodiment 16 is a device according to any one of embodiments 11 to 15, comprising a depth detecting unit adapted to the detect a depth of an ablation applied to the cut surface of the bone by the device.

Embodiment 17 is a device according to any one of embodiments 11 to 16, comprising an auto-focusing arrangement to automatically adjust a focus of the laser beam in relation to the cut surface of the bone.

Embodiment 18 is a device according to embodiments 16 and 17, wherein the auto-focusing arrangement is adapted to adjust the focus of the laser beam in accordance with the depth detected by the depth detecting unit.

Embodiment 19 is a device according to any one of embodiments 11 to 18, wherein the laser source is a solid-state Erbium laser source or, particularly, a solid-state Erbium-doped Yttrium Aluminium Garnet laser source.

Embodiment 20 is a method of preparing an osteotomy, comprising
obtaining data about a bone,
predefining an osteotomic geometry on the bone,
choosing an osteotomic instrument suitable for cutting the bone along the osteotomic geometry and for thereby generating a cut surface to the bone, and
allocating a timeframe and defining an environment
for preparing the bone in order to be accessible to the osteotomic instrument, and
for applying the osteotomic instrument to the bone thereby cutting the bone along the osteotomic geometry and generating a cut surface to the bone,
characterized by
allocating a further timeframe and defining the environment for delivering a laser beam to the cut surface of the bone after the cut surface is generated to the bone, and
arranging the environment in accordance with its definition in the allocated time frame.

Embodiment 21 is a method according to embodiment 20, wherein obtaining the data about the bone comprises analyzing the bone with computer tomography.

Embodiment 22 is a method according to embodiment 20 or 21, wherein the further timeframe is allocated and the environment is defined in accordance with delivering of the laser beam to the cut surface of the bone comprising ablating the cut surface of the bone.

Embodiment 23 is a method according to any one of embodiments 20 to 22, wherein the further timeframe is allocated and the environment is defined in accordance with delivering the laser beam to the cut surface of the bone comprising removing a layer of bone tissue at the cut surface of the bone.

Embodiment 24 is a method according to any one of embodiments 20 to 23, wherein the further timeframe is allocated and the environment is defined in accordance with the layer of the bone tissue having a thickness in a range of about one to about eight micrometer or, particularly, in a range of about two to about five micrometer.

Embodiment 25 is a method according to any one of embodiments 20 to 24, wherein the further timeframe is allocated and the environment is defined in accordance with delivering the laser beam to the cut surface of the bone comprising the laser beam applying lines of adjacent spots.

Embodiment 26 is a method according to embodiment 25, wherein the further timeframe is allocated and the environment is defined in accordance with delivering the laser beam to the cut surface of the bone comprising applying further lines of further adjacent spots wherein the further adjacent spots are offset and between the adjacent spots.

Embodiment 27 is a method according to embodiment 25 or 26, wherein the further timeframe is allocated and the environment is defined in accordance with the spots having a diameter in a range of about four hundred micrometer to about five millimeter or in a range of about four hundred micrometer to about one millimeter or in a range of about four hundred micrometer to about six hundred micrometer or, particularly, a diameter of about five hundred micrometer.

Embodiment 28 is a method according to any one of embodiments 20 to 27, wherein the further timeframe is allocated and the environment is defined in accordance with the laser beam being a pulsed laser beam.

Embodiment 29 is a method according to any one of embodiments 20 to 28, wherein the further timeframe is allocated and the environment is defined in accordance with the laser beam being generated by a solid-state Erbium laser device or, particularly, by a solid-state Erbium-doped Yttrium Aluminium Garnet laser device.

Embodiment 30 is a method according to embodiment 29, wherein the further timeframe is allocated and the environment is defined in accordance with the laser beam having a wavelength in a range of about two thousand nine hundred nanometer to about three thousand nanometer and particularly with a wavelength of about two thousand nine hundred and forty nanometer.

Embodiment 31 is a method according to any one of embodiments 20 to 30, wherein the further timeframe is allocated and the environment is defined in accordance with delivering the laser beam to the cut surface of the bone comprising cooling and hydrating the bone where the laser beam is applied.

Embodiment 32 is a method of manufacturing a device for treating a cut surface of a bone, comprising obtaining bone information about the bone and its cut surface; based on the gathered bone information, adapting a mounting structure of a support to be suitable to being connected to the bone such that the laser source is in a predefined position and orientation to the cut surface of the bone; equipping the support with a laser source for generating a laser beam such that the support carries the laser source; and equipping the device with the support.

The invention claimed is:

1. A method of cutting a bone, comprising:
preparing the bone in order to be accessible to an osteotomic instrument,
predefining an osteotomic geometry on the bone,
applying the osteotomic instrument to the bone thereby cutting the bone along the osteotomic geometry and generating a cut surface to the bone, wherein a smear layer is generated at the cut surface of the bone when applying the osteotomic instrument to the bone, and
delivering a laser beam configured to ablate the bone towards the cut surface of the bone such that the cut surface of the bone is ablated by the laser beam,
wherein delivering the laser beam to the cut surface of the bone comprises removing the smear layer at the cut surface of the bone.

2. The method according to claim 1, wherein the smear layer has a thickness in a range of about one to about eight micrometer.

3. The method according claim 1, wherein delivering the laser beam to the cut surface of the bone comprises the laser beam applying lines of adjacent spots.

4. The method according to claim 3, wherein delivering the laser beam to the cut surface of the bone comprises applying further lines of further adjacent spots wherein the further adjacent spots are offset and between the adjacent spots.

5. The method according to claim 3, wherein the spots have a diameter in a range of about four hundred micrometer to about five millimeter or in a range of about four hundred micrometer to about one millimeter.

6. The method according to claim 1, wherein the laser beam is a pulsed laser beam.

7. The method according to claim 1, wherein the laser beam is generated by a solid-state Erbium laser device.

8. The method according to claim 1, wherein the laser beam has a wavelength in a range of about two thousand nine hundred nanometer to about three thousand nanometer.

9. The method according to claim 1, wherein delivering the laser beam to the cut surface of the bone comprises cooling and hydrating the bone where the laser beam is applied.

10. The method according to claim 1, wherein the smear layer has a thickness in a range of about two to about five micrometer.

11. The method according to claim 5, wherein the spots have a diameter of about five hundred micrometers.

12. The method according to claim 8, wherein the laser beam has a wavelength of about two thousand nine hundred and forty nanometer.

13. The method according to claim 7, wherein the solid-state Erbium laser device is a solid-state Erbium-doped Yttrium Aluminium Garnet laser device.

* * * * *